(12) United States Patent
Bichler et al.

(10) Patent No.: US 12,239,562 B2
(45) Date of Patent: Mar. 4, 2025

(54) FOOT MOVEMENT LIMITING DEVICE AND SHOE

(71) Applicant: BETTERGUARDS TECHNOLOGY GmbH, Berlin (DE)

(72) Inventors: Vinzenz Bichler, Berlin (DE); Timo Stumper, Berlin (DE); Oscar Buschinger, Berlin (DE)

(73) Assignee: BETTERGUARDS TECHNOLOGY GmbH, Berlin (DE)

( * ) Notice: Subject to any disclaimer, the term of this patent is extended or adjusted under 35 U.S.C. 154(b) by 583 days.

(21) Appl. No.: 17/284,300

(22) PCT Filed: Oct. 9, 2019

(86) PCT No.: PCT/EP2019/077420
§ 371 (c)(1),
(2) Date: Apr. 9, 2021

(87) PCT Pub. No.: WO2020/074614
PCT Pub. Date: Apr. 16, 2020

(65) Prior Publication Data
US 2021/0378854 A1    Dec. 9, 2021

(30) Foreign Application Priority Data
Oct. 9, 2018   (DE) ............... 10 2018 124 932.2

(51) Int. Cl.
*A61F 5/00*    (2006.01)
*A43B 7/14*    (2022.01)
(Continued)

(52) U.S. Cl.
CPC .............. *A61F 5/0127* (2013.01); *A43B 7/14* (2013.01); *A43B 7/20* (2013.01); *A61F 2005/0169* (2013.01)

(58) Field of Classification Search
CPC ...... A61F 5/0104; A61F 5/0111; A61F 5/019; A61F 5/0123; A61F 5/01; A61F 5/058;
(Continued)

(56) References Cited

U.S. PATENT DOCUMENTS 1,666,290 A * 4/1928 Johnston ............... A61F 5/0111
602/65
3,295,517 A * 1/1967 Stevens ................. A61F 5/0104
2/22
(Continued)

FOREIGN PATENT DOCUMENTS

DE    8700201 U1    2/1987
DE    4318588 C1    8/1994
(Continued)

OTHER PUBLICATIONS

German Office Action for corresponding German application DE 10 2018 124 932.2, 6 pages, dated Sep. 2, 2019.
(Continued)

*Primary Examiner* — Adam Baker
(74) *Attorney, Agent, or Firm* — Ruggiero McAllister & McMahon LLC

(57) ABSTRACT

A foot movement limiting device for limiting a foot movement via the ankle joint, and to a correspondingly configured shoe for limiting a foot movement via the ankle joint. The foot movement limiting device includes a support arrangement for supporting on a lower leg or from proximally on the ankle bone, a retaining arrangement for retention on a foot and at least one attachment element for limiting a relative movement between the support arrangement and the retaining arrangement.

18 Claims, 14 Drawing Sheets

(51) Int. Cl.
*A43B 7/20* (2006.01)
*A61F 5/01* (2006.01)

(58) Field of Classification Search
CPC .. A61F 5/0585; A61F 5/05858; A61F 5/3723; A61F 5/373; A61F 5/0127; A61F 5/013; A61F 5/0566; A61F 5/3715; A61F 2005/0169; A61F 2005/0179
USPC .......................................................... 602/27
See application file for complete search history.

(56) References Cited

U.S. PATENT DOCUMENTS

| | | | |
|---|---|---|---|
| 4,753,229 | A | 6/1988 | Sutherland |
| 4,815,731 | A | 3/1989 | Suarez et al. |
| 5,277,699 | A | 1/1994 | Williamson |
| 5,382,224 | A | 1/1995 | Spangler |
| 5,472,411 | A | 12/1995 | Montag et al. |
| 6,126,625 | A | 10/2000 | Lundberg |
| 7,458,950 | B1 * | 12/2008 | Ivany ....................... A43B 7/14 602/5 |
| 9,579,221 | B2 | 2/2017 | Mosler et al. |
| 9,877,540 | B2 | 1/2018 | Fleuren |
| 2003/0204971 | A1 | 11/2003 | Fauver |
| 2004/0043879 | A1 | 3/2004 | Huang |
| 2005/0198869 | A1 | 9/2005 | Bouche et al. |
| 2007/0287615 | A1 | 12/2007 | Gilchrist |
| 2008/0077066 | A1 | 3/2008 | Lewis |
| 2012/0029401 | A1 | 2/2012 | Caldwell et al. |
| 2015/0173926 | A1 | 6/2015 | Bichler |
| 2016/0095735 | A1 * | 4/2016 | Wenger ................. A61F 5/0113 602/28 |
| 2016/0113802 | A1 | 4/2016 | Zaccaria |
| 2016/0270943 | A1 | 9/2016 | Forrey et al. |
| 2018/0042752 | A1 | 2/2018 | Omarsson et al. |

FOREIGN PATENT DOCUMENTS

| | | |
|---|---|---|
| DE | 102008008281 | 3/2016 |
| DE | 102017109877 A1 | 11/2018 |
| EP | 0824014 A1 | 2/1998 |
| WO | 2012169895 A2 | 12/2012 |
| WO | 2020074614 A1 | 4/2020 |

OTHER PUBLICATIONS

International Search Report for corresponding International (PCT) application No. PCT/EP2019/077403, 5 pages, dated Jan. 14, 2020.
International Search Report for International (PCT) application No. PCT/EP2019/077420, 5 pages, dated Jan. 14, 2020.
Chinese Office Action for corresponding Chinese application CN 201980080020.5, 12 pages, dated Jan. 30, 2022.
Korean Office Action for corresponding Korean application KR10-2021-7013852, 15 pages, dated Jul. 8, 2022.

* cited by examiner

FOOT MOVEMENT LIMITING DEVICE AND SHOE

TECHNICAL FIELD

The present disclosure relates to a foot movement limiting device for limiting a foot movement via the ankle joint, and to a correspondingly configured shoe for limiting a foot movement via the ankle joint.

DESCRIPTION OF THE RELATED ART

It is known to stabilize the movement of the ankle joint by means of devices for limiting foot movements, in order to counteract trauma caused by an ankle sprain, that is to say a movement of the ankle joint over at least one of its ankle joint axes in a non-physiological range. The most frequent form of sprain injury is an ankle joint distortion as a stretching or tearing following an inversion. On account of the increasing inversion angle, inversion movements over an ankle joint axis result in a change of the distance between foot and lower leg. When a defined inversion angle or a defined inversion speed or inversion acceleration is exceeded, damage to the ligaments of the ankle joint or tears can occur.

To prevent this, devices are known which permit movements within a defined range and which, starting from a defined limit angle of the movement about the ankle joint axis, completely prevent movement. For this purpose, relatively rigid orthoses are known in which movements are inhibited mainly by use of splints or splint plates.

Moreover, devices or shoes are known in which a movement of the ankle joint is permitted as far as a defined limit angle of the movement and in which, on account of the structure, a movement is completely blocked starting from this limit angle. Such a device is known, for example, from EP 2 717 809 B1.

Devices are also known which, when fitted, always allow a minimum amount of movement but block in the event of dangerous movements. DE 10 2014 107 335 A1 discloses a device for adaptive limitation of an inversion or supination movement via the ankle joint. In order to prevent the upper part of the orthosis from moving in the direction of the foot in the event of an exertion of force originating from the foot, the ankle joint orthosis disclosed therein requires, in order to support the receptacle of the upper region, a pressure-stable bar which is located on the medial side of the ankle joint and which extends between the upper region of the orthosis and the lower region of the orthosis and which has to be fixedly connected to both regions. The bar has to be configured in such a way that the tensile forces introduced into the upper region via the pull-out device on the lateral side are returned by it to the lower region as compressive forces on the medial side without deforming or buckling. This secures a position in the distal direction. However, the bar on the medial side of the foot still limits the freedom of movement of the ankle joint.

Instead of the aforementioned support between upper and lower part, it is moreover known to provide on the upper part a fixing means for fixing the upper part to a lower leg. With the fixing means, the upper part is in this case supported from above on the ankle bone. On account of the supporting and fixing means, these devices have a heavy weight and a relatively rigid structure and poor wearing comfort.

More recent devices or shoes are also known in which a support arrangement is provided which bears on the lower leg, by means of a circumferential band being turned back in an eyelet, tightened and then fixed. By way of a damping element for damping a relative movement, this support arrangement is connected to a retaining arrangement for retention on a foot. At least at one end, the damping element is at all times fixedly connected to the shoe or to the device. Moreover, after the device or shoe has been fitted, a pretensioning arrangement always has to be pretensioned by hand in order, in the fitted state on a foot, to provide a pretensioning of the damping element and a sufficient action of the damping element and therefore of the device or the shoe.

The above-stated devices must however, in order to be able to fully perform their function, be adapted to the dimensions of the lower leg of the wearer. If individual constituent parts of the device, in the fitted state, are not situated in their intended position on the body of the wearer, this can reduce the protective effect of the device. In the extreme case of unsuitable positioning, the protective function may even fail entirely.

This problem has hitherto been counteracted through the provision of limiting devices of different sizes or by means of individual adaptations. Specifically for the case in which the limiting devices are intended to be integrated into shoes, this constitutes a particular problem, because now not only the shoe size but also the dimensions of the lower leg of the wearer are of importance.

BRIEF DISCLOSURE

It is an object of the present disclosure to make available an improved foot movement limiting device for limiting a foot movement via the ankle joint.

The object is achieved by a foot movement limiting device for limiting a foot movement via the ankle joint having the features of claim 1. Advantageous developments are set forth in the dependent claims, the description and the figures.

Accordingly, a foot movement limiting device is proposed for limiting a foot movement via the ankle joint, comprising a support arrangement for supporting on a lower leg or from proximally on the ankle bone, a retaining arrangement for retention on a foot, preferably on a sole region, and at least one attachment element for limiting a relative movement between the support arrangement and the retaining arrangement, wherein the at least one attachment element is attached to the support arrangement at two different attachment points, and the at least one attachment element is, at one point, held by means of an articulated mounting on the retaining arrangement, wherein the articulated mounting is configured in such a way that the attachment element is attached to the retaining arrangement so as to be displaceable relative to the latter within a predefined range. Furthermore, the support arrangement comprises a stretch-resistant region extending posteriorly around from a lateral side, from the first attachment point, at least to a medial side, to the second attachment point, or the support arrangement comprises a stretch-resistant region extending anteriorly around from a lateral side, from the first attachment point, at least to a medial side, to the second attachment point.

According to the disclosure, the stretch-resistant region is connected at its ends by a stretch-elastic region, wherein the stretch-elastic region preferably extends between the first attachment point and the second attachment point counter to the stretch-resistant region.

By virtue of the fact that the stretch-resistant region is connected at its ends by a stretch-elastic region, the support region on the body of the person wearing the foot movement limiting device can be held in position by the stretch-elastic region. In this way, it can be ensured that the foot movement limiting device can be worn by users with different leg circumferences, in particular different ankle circumferences ankle bone circumferences, in the region above the ankle bone. The components of the foot movement limiting device can, owing to the flexible region, always be held in position such that the potential of the foot movement limiting device can be fully exploited. Improper positioning attributable to the physical dimensions of the user, in particular to the ankle circumferences and ankle bone circumferences, can thus be counteracted.

Furthermore, the stretch-elastic region can at least partially provide a pretensioning, which in turn can have an increasing influence on the stiffness of the support arrangement.

For this purpose, the stretch-elastic region has, in the unloaded state, a length which, in conjunction with the length of the stretch-resistant region, as viewed in a circumferential direction of the lower leg, forms a circumference of the support arrangement which is smaller than a predefined minimum ankle circumference for which the device is configured. In this way, in the fitted or worn state of the foot movement limiting device on a foot, the stretch-elastic region undergoes stretching which effects the pretensioning of the stretch-elastic region.

Alternatively, the stretch-elastic region may also, at one end, be attached by means of an eyelet and a loop to the corresponding end of the tension-resistant region, wherein a pretensioning of the stretch-elastic region is preferably adjustable by means of an adaptation of the loop length. Furthermore, the tension-resistant region may, at at least one end, have a series of eyelets arranged spaced apart from one another in a circumferential direction, wherein a hook fastened to an end of the stretch-elastic region can be hooked into one of the eyelets. Alternatively, the stretch-elastic region may also have an eyelet and the stretch-resistant region may, at its end, have a series of hooks.

Furthermore, through the provision of the stretch-elastic region, an adaptation to different ankle bone circumferences and ankle circumferences can be facilitated. By means of the stretch-elastic region, the support region can be adapted, at least between a predefined minimum theoretical ankle circumference and a maximum theoretical ankle circumference, to the ankle of the person wearing the device. Consequently, the foot movement limiting device is suitable for persons with different ankle circumferences without the device requiring adaptation. Furthermore, despite the fact that every person has a lower extremity of different form, the support device can fit the device in a substantially accurately fitting manner onto the ankle region of the person.

Furthermore, by means of the stretch-elastic region that extends between the ends of the stretch-resistant region, stepping into the foot movement limiting device can be made possible, in particular if the foot movement limiting device is a constituent part of a shoe, of a bandage or of a sock or is formed as an orthosis.

By virtue of the fact that the support arrangement comprises a stretch-resistant region extending posteriorly around from a lateral side, from the first attachment point, at least to a medial side, to the second attachment point, the foot movement limiting device is suitable for the protection of at least one outer ligament of the user, in particular the anterior tibiofibular ligament and/or the fibiocalcaneal ligament, if the articulated mounting is arranged at a lateral side of the ankle joint.

Alternatively or in addition, according to a further embodiment, the foot movement limiting device may be designed such that a support arrangement comprises a stretch-resistant region extending posteriorly around from a medial side, from the first attachment point, at least to a lateral side, and preferably anteriorly around back to the medial side, to the second attachment point. This may be advantageous in particular if the articulated mounting is arranged at a medial side of the foot movement limiting device, particularly for protection of an inner ligament of the ankle joint.

By virtue of the fact that the at least one attachment element is held in an articulated manner at one end on the retaining arrangement, and the attachment element is attached to the support arrangement, preferably movably, it is made possible that the attachment element can move relative to the foot during a movement of the foot relative to the lower leg via the ankle joint. In other words, the attachment element can move about the articulated mounting, such that the orientation of the attachment element relative to the lower leg and the front of the foot, when the foot movement limiting device is fitted on a foot, can change its relative position. In this way, the freedom of movement of the foot is greatly increased, since an attachment element secured fixedly to the device at least at one end provides a structural stiffening of the device, which is avoided by the articulated mounting.

Moreover, by virtue of the fact that it is always able to realign itself during a movement of the foot via the ankle joint, the attachment element can align more closely to an optimal force transmission direction which is obtained during an inversion on account of the restoring force between support arrangement and retaining arrangement. This therefore has the effect on the one hand that the attachment element can provide particularly efficient retention.

Therefore, compared to conventional devices, a foot movement limiting device configured in this way can provide an improved protective effect and at the same time an improved freedom of movement and enhanced wearing comfort.

It has been found that separate tightening and fixing of the support arrangement to the lower leg is not necessary, and a protective effect for the ankle joint is provided even without such a measure.

The term "foot movement limiting device" refers to a device which, when worn or fitted on a foot, at least a movement in at least one (complex) movement direction up to a predefined value or predefined extent of the movement is allowed, preferably without significant restriction of freedom of movement. Above the predefined value or predefined extent of the movement, the device causes a restriction of the movement. The extent of movement in said at least one movement direction is consequently limited by the device.

The terms lateral, medial, posterior, anterior, proximal, distal, dorsal and plantar are to be understood as corresponding to the anatomical directional designations when the foot movement limiting device or the shoe is fitted correctly on a foot.

In the present case, therefore, the term "lateral side" comprises an outer side of the foot movement limiting device. Here, the lateral side of the foot movement limiting device corresponds to a lateral side of a human foot or of a lower human extremity when wearing the shoe.

In the state when the foot movement limiting device is being worn, the "lateral side" is directed to the side, or away from the center of the body of the wearer. In other words, the term "lateral side" comprises a lateral side of the human body within the meaning of (topographic) anatomy.

Accordingly, in the present case, the term "medial side" comprises an inner side of the foot movement limiting device. The medial side of the foot movement limiting device corresponds to a medial side of a human foot or of a lower human extremity when wearing the foot movement limiting device. In the state when the foot movement limiting device is being worn, the "medial side" is oriented towards the center of the body or located in the center. In other words, the term "medial side" comprises a medial side of the human body within the meaning of (topographic) anatomy.

Moreover, the term "dorsal" corresponds to an upper face of the foot, the term "plantar" corresponds to an underside of the foot, the term "proximal" denotes facing or located towards the center of the body, and the term "distal" denotes facing or located away from the center of the body.

A "heel region" comprises a region of the foot movement limiting device or of a shoe in which, in the state when being worn, a heel of a foot is received. Therefore, the heel region corresponds to a rear or posterior side of the foot movement limiting device within the meaning of the (topographic) anatomy of the human body. Consequently, the heel region of the shoe lies opposite an anterior side.

Here, "stretch-resistant" is to be understood as any material with which tensile forces can be transmitted. Within the meaning of the application, stretch-resistant materials can have a certain initial expansibility and, starting from a certain expansion limit value or extension limit value, preferably stiffen in such a way that the expansibility is then greatly reduced compared to the initial expansibility or extensibility. In the present case, a textile braid of filaments of a stretch-resistant material can be used as a stretch-resistant band, wherein a tensile load placed on the textile braid initially causes the filaments of the textile braid to orient themselves increasingly in the longitudinal extent of the textile braid, such that a high initial expansibility is made available at the outset by the orientation of the filaments, and, after the filaments are oriented substantially in the force flow direction, the band has a stretch-resistant structure. Alternatively, the material can also have a stretch-resistant behavior substantially directly.

In the present case, the term "ankle joint" comprises the upper and the lower ankle joint and, accordingly, the movement axis of the upper ankle joint, which substantially permits the plantar flexion and dorsal extension of the foot, and the movement axis of the lower ankle joint, which substantially permits inversion and eversion, and also supination, adduction and plantar flexion, abduction and dorsal extension.

Here, the term "ankle bone" is moreover understood as the eminence of the joint socket, the ankle mortise of the upper ankle joint. Consequently, the term "ankle bone" in the present case comprises the lateral malleolus and the medial malleolus. By virtue of the configuration of the ankle mortise as joint socket, the ankle bone has, with respect to the proximal-distal direction, a greater cross-sectional surface area compared to the portion of the lower leg that adjoins above, and therefore proximally. Therefore, the circumference of the ankle bone is greater compared to the proximally adjoining portion.

Here, an articulated mounting or the term "held in an articulated manner" is understood in particular as meaning that the attachment element has at least one degree of freedom at a connection site to the retaining arrangement. The attachment element is preferably pivotable about a pivot axis, preferably at least in a predefined angle range.

The term "band" is understood in particular as an elongate element which on the one hand is stretch-resistant, and therefore can transmit tensile forces, and on the other hand is pliable or flexible transversely with respect to the longitudinal extent of the band, such that it can be placed transversely to its longitudinal extent onto a corresponding structure. Moreover, a band can be easily turned back. In the present case, the term band generally comprises an elongate, flexurally slack, optionally elastic element, which can have the form of an individual fiber, a fiber strand, a wire, a cord, a cable, a textile woven fabric with limited width and fixed weave edges at both sides, or similar.

According to a further embodiment, the at least one attachment element is attached to the support arrangement at two different attachment points, preferably movably, particularly preferably displaceably. The damping element can thus always move along the attachment element within the two attachment points and thus, during movements of the foot via the ankle joint, can always adopt the above-described favorable or even optimal orientation.

It has been found that, when the at least one attachment element preferably extends from one attachment point to the other attachment point, and the attachment element is, between the two attachment points, held displaceably on the retaining arrangement, the abovementioned effect can be achieved in a particularly pronounced manner.

The attachment element is preferably made available as an elongate, stretch-resistant element, preferably in the form of a band, a lace, a yarn, a cable, a wire and/or a knit, preferably a textile knit.

An embodiment has furthermore proven advantageous in which the attachment points are positioned relative to the attachment element in such a way that a retaining force arising in the attachment element as a result of a foot movement via the ankle joint is divided into a laterally and proximally acting component and a medially and proximally acting component. In this way, it is in particular possible for the retaining force generated by the attachment element to be introduced into the support arrangement to both sides of the foot or lower leg of a person wearing the foot movement limiting device, such that, opposite the attachment element, the support arrangement bears on the lower leg or ankle bone in the form of a linear load. In other words, the supporting action is obtained by the support arrangement being pulled at both ends, and the support arrangement can thus bear on the ankle bone substantially without being displaced.

In a further embodiment, the at least one attachment element is held by way of a damping element on the support arrangement or the retaining arrangement.

In relation to conventional devices, the damping element can be dimensioned so as to be even smaller, because the damping effect or damping force provided by the damping element can be optimally utilized.

It has been found that, owing to the abovementioned improved orientation of the damping element and the improved protective effect of the damping element, it is even possible to dispense with manual pretensioning of the damping element.

A "damping element" is understood as a device which, in a speed-dependent or acceleration-dependent manner, damps a relative movement between two components of the damping element. Therefore, a relative movement between the support arrangement and the retaining arrangement is damped by the damping element in a speed-dependent or acceleration-dependent manner.

The damping element is preferably provided here as an adaptively damping element. In other words, below a predefined limit speed or limit acceleration, the damping element has a preferably low first damping constant, and, starting from or above the predefined limit speed or limit acceleration, a preferably higher damping constant. It is thereby possible that, below the predefined limit speed or limit acceleration, the damping element has a lower damping effect, according to the ratio of the damping constants, than it does above the limit speed or limit acceleration. It has been found that in this way, particularly during movements with moderate speeds or accelerations, an almost unimpeded mobility of the ankle joint can be made available. If an inversion occurs with high speeds and/or accelerations at which there is a danger of injuries to the ligaments of the ankle joint, the foot movement limiting device damps the inversion movement via the damping element, and injury is avoided.

In a refinement, the damping element is fastened to the stretch-resistant region of the support arrangement.

In a further embodiment, the damping element is held displaceably on the at least one attachment element, wherein the damping element is attached to the attachment element between the two attachment points.

According to a further embodiment, a plurality of attachment elements are provided, preferably two attachment elements. This in particular results in an especially favorable geometry with respect to a transmission of force or forwarding of force from the damping element into the attachment elements and onwards into the support arrangement. The damping force which is generated by the damping element, and which acts substantially in the direction of the central spline, can thus be transmitted in part, depending on the orientation, to the preferably two attachment elements. Each of the attachment elements preferably extends from one attachment point to another attachment point, wherein the damping element is attached, preferably displaceably, to the respective attachment element between the two attachment points. The individual attachment elements can each have their own attachment points or can meet each other at common attachment points.

Preferably, a first attachment element, relative to a central spline, preferably a central axis, of the damping element is attached preferably slidably to the damping element, at a distance from the central spline, preferably from the central axis, on a first side, and the second attachment element, relative to the central spline, preferably the central axis, of the damping element is attached preferably slidably to the damping element, at a distance from the central spline, preferably from the central axis, on a second side. This structure leads to further improved alignability of the damping element so that it can orient itself as closely as possible and as directly as possible in the force direction.

If the distance of the attachments from the first attachment element and second attachment element to the damping element is substantially identical relative to the central spline, preferably to the central axis, then the oppositely acting moments over the distance of the attachments with respect to the central spline are also similarly high. This therefore permits a particularly efficient orientation of the damping element in the direction of a direct force flow direction.

In order to further simplify the structure of the foot movement limiting device, it is possible, according to a further embodiment, that the first attachment element and the second attachment element are configured as an individual part, wherein the individual part is then deflected and guided slidably at the first attachment point or the attachment point.

It has been found that, if a pocket is provided for at least partially receiving the attachment element and/or the damping element, wherein the attachment element and/or damping element received in the pocket is arranged in the pocket in such a way as to be movable relative to the latter, the mobility of the damping element relative at least to the retaining arrangement is made easier. In other words, the pocket can at least partially provide a space for the free movement of the damping element. Moreover, the pocket can function as a protector for at least parts of the damping element. A pocket in the shape of a triangle or trapezoid widening in the proximal direction has proven particularly advantageous.

In order to achieve the free mobility of the damping element in the pocket, the pocket can preferably have a material with a low coefficient of friction, wherein the pocket is preferably connected to the retaining arrangement. The pocket preferably has an aramid, preferably PPTA, or a polyolefin, preferably PTFE, or the material of the pocket has, at least in part, a low-friction coating. Low-friction coatings are known per se.

According to a further embodiment, a sheath is provided which at least partially encloses the damping element and preferably the at least one attachment element, wherein the sheath is preferably at least partially arranged inside the pocket, movably relative to the pocket. In this way, it is possible among other things to enhance the protection of the damping element or of sensitive components of the damping element. Moreover, the sheath can preferably provide a positioning of the damping element and of the at least one attachment element relative to each other.

According to a further embodiment, the articulated mounting can be configured as a pivot joint and/or ball joint, which is arranged at a fixed location of the retaining arrangement. This has the effect that, in a state in which the device is fitted onto a foot, in a predefined position with respect to the foot, the force introduction from the attachment element into the retaining arrangement is always transmitted into the retaining arrangement and by way of the latter into the foot. The position is preferably chosen such that the force direction of a retaining force made available by the device is aligned with an inversion movement or a supination movement.

Alternatively or in addition, the articulated mounting can be configured in such a way that the attachment element is attached to the retaining arrangement so as to be displaceable relative to the latter within a predefined range.

An optional embodiment of the articulated mounting that has proven particularly advantageous is one in which the retaining arrangement has a band which is fastened to the retaining arrangement at two locations spaced apart from each other and thus forms an eyelet or loop. Here, the attachment element is held on the band preferably via an eyelet or loop through which the band runs. Alternatively, the attachment element may also be guided directly in the band, or the retaining arrangement has an eyelet through which the attachment element runs and is thus guided. In this way, the attachment element can move at least partially along the band or the eyelet relative to the retaining arrangement. Moreover, in this embodiment, it is possible that the attachment element can be pivoted relative to the retaining arrangement.

Preferably, an opening of the support arrangement can be adjusted via the loop formation. In a loose state of the loop, the support arrangement can thus be easily fitted in place. After the support arrangement has been brought over the ankle bone, to its position posterior to the latter, the support arrangement can be applied tightly to the lower extremity of the person wearing the foot movement limiting device and fixed by tightening the loop via the eyelet.

According to a further embodiment, the damping element has a receptacle which is filled with a damping medium, preferably a damping fluid, and in which a pull-out body is received movably relative to the latter, wherein the pull-out body is connected to a tensioning element extending in a pull-out direction from the receptacle, wherein the receptacle is preferably arranged proximally and the tensioning element extends distally from the receptacle, wherein the tensioning element is connected in an articulated manner to the retaining arrangement, wherein the attachment of the at least one attachment element to the receptacle is preferably arranged at a distal end of the receptacle. During a relative movement of the pull-out body, and of the tensioning element secured thereon, with respect to the receptacle, the movement of the tensioning element can be damped in accordance with the geometry of the inside of the receptacle and of the pull-out body and also in accordance with the nature, in particular the viscosity, of the damping medium.

If the damping element has a receptacle in the form of a tubular first damper part, and a tensioning element in the form of a second damper part that is movable relative to the first damper part along a pull-out direction extending along the longitudinal axis of the tubular first damper part, wherein the second damper part extends partially in the interior of the tubular first damper part and has the pull-out body therein, and wherein a damping medium is moreover contained in the damping element, this has proven an advantageous embodiment. During a relative movement of the second damper part with respect to the first damper part, the movement of the second damper part can be damped in accordance with the geometry of the inside of the first damper part and of the pull-out body of the second damper part and also in accordance with the nature, in particular the viscosity, of the damping medium.

In order to provide further improved positional accuracy of the support arrangement, a volume body, preferably a pad, can be arranged above the lateral malleolus, preferably on the stretch-resistant region, for bearing proximally on the lateral malleolus, and/or a volume body, preferably a pad, can be arranged above the medial malleolus, for bearing proximally on the medial malleolus.

According to a further embodiment, the damping element is arranged substantially distally from the ankle bone. Here, distally from the ankle bone is to be understood as meaning that, when the foot movement limiting device is fitted or pulled onto a foot, the damping element is located distally from the ankle bone.

According to a further embodiment the the device attached to a stocking, sock of a bandage or of an orthosis.

The abovementioned object is moreover achieved by a shoe for limiting a foot movement via the ankle joint, having the features of claim 13. Advantageous developments are set forth in the dependent claims, the description and the appended figures.

Accordingly, a shoe for limiting a foot movement via the ankle joint is proposed, comprising a sole region and, attached to the sole region, a shoe upper. According to the disclosure, the shoe has a foot movement limiting device according to any of the preceding embodiments.

Since the shoe has a foot movement limiting device according to any of the preceding embodiments, the advantages and effects described with respect to the foot movement limiting device can be achieved analogously.

Moreover, this means that a person wishing to protect his ankle joint or the ligaments thereof does not have to put on a foot movement limiting device and additionally a shoe, and instead he can obtain the protective effect by putting on a suitably configured shoe that already comprises the foot movement limiting device.

Here, a "shoe" is understood as any form of shoe-like foot apparel with an upper or shaft and, connected to the latter, a solid base or sole, in particular orthopedic shoes, sports shoes, leisure shoes and boots or sandals. The shoe upper and/or the sole can have an uninterrupted surface, or they can simply have segments that are needed for retention and force transmission in the event of inversion or supination of the foot. The shoe can likewise have as its main structure a sock or a stocking made of a woven textile fabric or knitted textile fabric, on at least partial regions of which are arranged segments on the shoe upper and/or on the sole by means of which the forces needed for retention of the foot in the event of inversion or supination can be taken up and passed on.

According to a further embodiment, the retaining arrangement is integrated in the sole region and/or the support arrangement is integrated in a shaft region of the shoe, wherein the attachment element is movable relative to the shoe upper. By virtue of the integration of support arrangement and/or retaining arrangement in the shoe, it is possible to achieve a particularly compact structure of the shoe. By providing the mobility of the attachment element relative to the shoe upper, it is possible in particular that the attachment element can move relative to the shoe upper during a movement of the foot about the ankle joint, which corresponds to a change of the relative position of the foot to the lower leg and likewise to the ankle bone, in order thereby to adopt the above-described orientation located near a direct force flow direction which, in the event of inversion between foot and lower leg, acts on the ligaments of the ankle joint or on the ankle joint. As has already been described above with reference to the foot movement limiting device, the mobility of the foot, hence the wearing comfort for the person wearing the shoe, is enhanced thereby. Moreover, by virtue of the possibility that the attachment element aligns itself close to or in the direct force direction, the protective effect that can be provided via the foot movement limiting device is increased by comparison with conventional shoes, without this significantly impairing the mobility via the ankle joint.

If the foot movement limiting device is integrated substantially completely in the shoe, the visual aspect of the shoe can be substantially maintained in relation to an embodiment without a foot movement limiting device. Since shoes are purchased increasingly according to their outward appearance, this has among other things the advantage that persons who consider the outward appearance of a shoe to be desireable can likewise turn to a shoe with a foot movement limiting device, without in so doing having to accept any subjective optical or esthetic deficits.

Moreover, by virtue of the complete integration of the foot movement limiting device in the shoe, it is possible to obtain particularly good protection of the foot movement limiting device or of the components thereof. Furthermore, a very high positional accuracy of support element, retaining element, attachment element and optionally damping element relative to the shoe can be achieved.

In shoes in which the upper is substantially completely stretch-resistant, for example walking shoes, safety shoes or high-shaft sports shoes, for example basketball shoes, the resulting increase of the distance from the front of the foot to the region above the ankle bone has the effect that, in the event of inversion, the shaft is pulled down at and above the ankle bone in the direction of the front of the foot, i.e. in the distal direction. Because of this, a connection of the shaft to the body region proximally of the ankle bone is necessarily released. Therefore, according to a further embodiment, the shoe, preferably at least in a shaft region of the shoe upper below the support arrangement, has a flexible deformation portion in order to permit a relative movement of the support arrangement relative to the retaining arrangement. By means of this flexible deformation portion, it is possible that, in a movement via the ankle joint, the support arrangement and the retaining arrangement at the respective portions of the lower extremity are positioned substantially in the predefined and intended position and remain connected thereto. In other words, the contact of the support arrangement to the lower leg and upper ankle region does not tear off for example in the event of inversion, since the flexible deformation portion permits the relative movement described above.

According to a further embodiment, the pocket is connected fixedly to the shoe upper and is preferably integrated in the shoe upper. In this way, the movement space for the attachment element and optionally the damping element relative to the shoe upper can be precisely predefined. Moreover, a simple integration of the foot movement limiting device into the shoe is permitted.

It has proven particularly advantageous if the attachment element and/or optionally the damping element is arranged substantially distally from the ankle bone. It is in this way possible, among other things, to reduce an absolute height of the shaft of the shoe by comparison with shoes in which for example a damping element is arranged at the height of the ankle bone or even above the latter. For example, instead of a conventional high-cut shoe, it is thus possible to make available a mid-cut shoe offering the same or an even better protective effect, wherein, in addition to the esthetically more pleasing shape of the last-mentioned shoe, the wearing comfort can also be enhanced.

According to a further embodiment, a window, preferably a viewing window, is provided which is configured in such a way that a view of at least a part of the attachment element and/or of the damping element is obtained from outside the shoe. The window can be used, for example, to allow a person to visually check the attachment element and/or the damping element, or it can even facilitate replacement or maintenance at least of parts of the attachment element and/or of the damping element. The window can at least partially have a transparent material and/or can have a region in which no material at all is provided.

The damping element is preferably configured here in such a way that the operating principle of the damping element is clearly evident. Preferably, the receptacle of the damping element has a transparent region providing a view into the interior of the receptacle.

The window can preferably comprise an outer material of the shoe, preferably of the shoe upper, a region of the pocket and/or a region of the sheath. In other words, the outer material of the shoe, the region of the pocket and/or the region of the sheath can have a window or an opening.

BRIEF DESCRIPTION OF THE FIGURES

Preferred further embodiments of the disclosure are explained in detail in the following description of the figures, in which.

DETAILED DESCRIPTION OF ILLUSTRATIVE EMBODIMENTS

Preferred illustrative embodiments are described below with reference to the figures. Elements that are identical or similar or that have an identical action are provided with identical reference signs in the different figures, and the description dispenses to some extent with repeated description of these elements in order to avoid redundancy.

Figure 1:
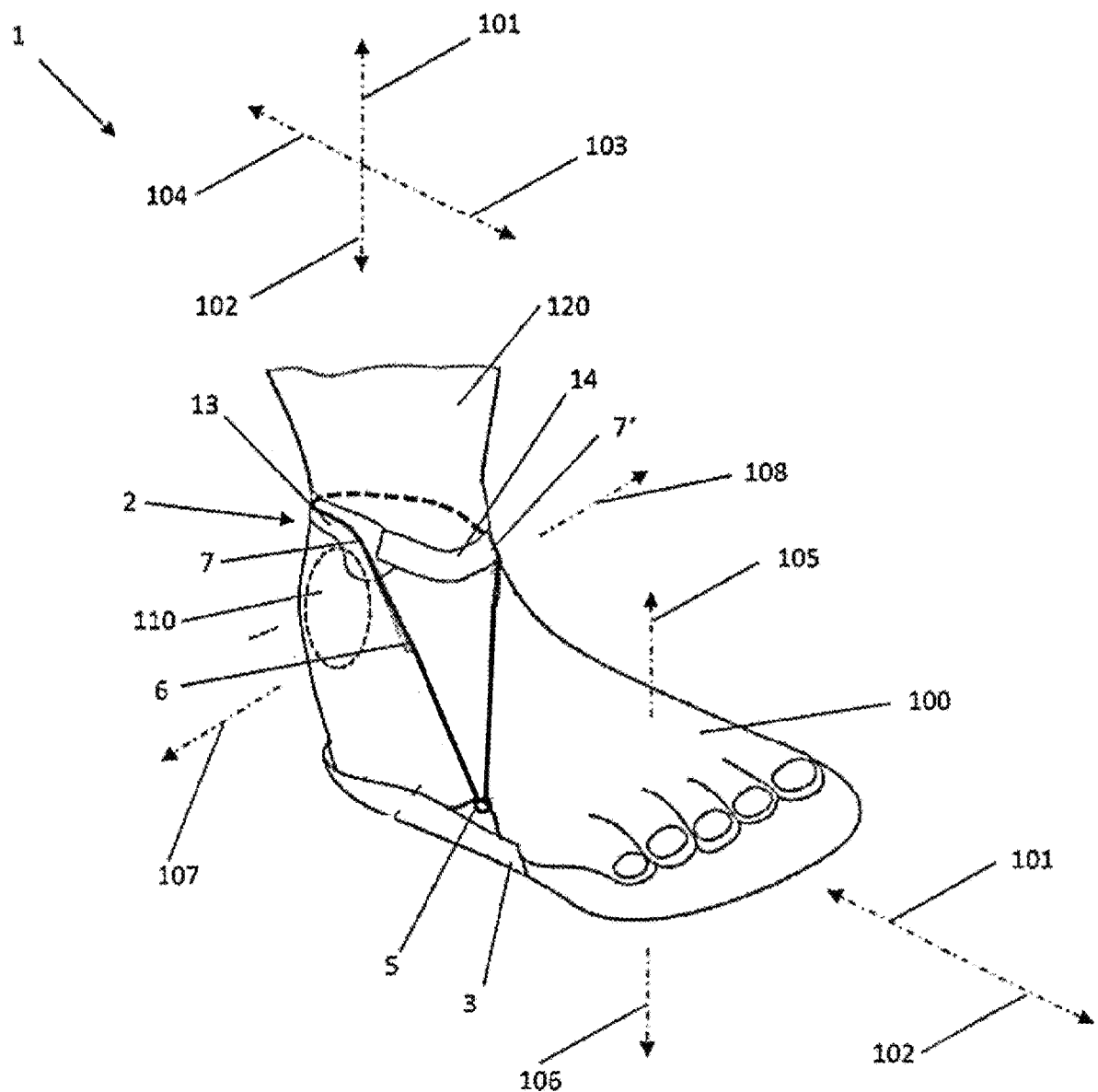
FIG. 1 shows a schematic perspective side view of a foot movement limiting device for limiting a foot movement via the ankle joint, according to a first embodiment.

FIG. 1 shows a schematic perspective side view of a foot movement limiting device 1 for limiting a foot movement via the ankle joint, according to a first embodiment, which is placed on a foot 100.

For better understanding, the reference signs 101-108 indicate the anatomical directions with respect to the ankle joint, and these apply analogously below in the description of the foot movement limiting device 1. Accordingly, the reference signs denote the following: 101 proximal, 102 distal, 103 posterior, 104 anterior, 105 dorsal, 106 plantar, 107 lateral and 108 medial.

The foot movement limiting device 1 has a support arrangement 2 for supporting from proximally 101 on the ankle bone 110 of the ankle joint. Moreover, it has a retaining arrangement 3 for retention on a sole region of the foot 100. Arranged between the support arrangement 2 and the retaining arrangement 3 is an attachment element 6, by means of which a relative movement between the support arrangement 2 and the retaining arrangement 3 can be limited.

At its distal end, the attachment element 6 is held in an articulated manner on the retaining arrangement 3 via an articulated mounting 5. Consequently, the attachment element 6 is movable, about the articulated mounting 5, relative to the retaining arrangement 3 and thus also to the foot 100. In other words, the attachment element 6 is mounted displaceably on the mounting 5.

According to FIG. 1, the attachment element 6 is configured as a stretch-resistant band and is attached to the support arrangement 2. The attachment element 6 extends from the support arrangement 2, from a first attachment point 7, via the mounting 5 to a second attachment point 7', at which it is again attached to the support arrangement 2.

If a position of the foot 100 relative to the lower leg 120 changes through a movement via the ankle joint, then the attachment element 6, on account of the provided free mobility relative to the retaining arrangement 3, in particular via the displaceable attachment to the mounting 5, is able to align itself anew relative to the support arrangement 2 according to the change of the foot position.

The support arrangement 2 has a stretch-resistant region 13 which extends from the lateral side, starting from the first attachment point 7, posteriorly around and across a heel region of the foot 100, to the second attachment point 7' on the medial side. The attachment points 7, 7' are positioned in such a way that a retaining force acting on the mounting 5 as a result of a foot movement via the ankle joint is divided via the attachment element 6 into a laterally and proximally acting component and a medially and proximally acting component.

Between the two attachment points 7, 7', a stretch-elastic region 14 extends anteriorly 103. The stretch-elastic region 14 is configured in such a way that, when the foot movement limiting device 1 is fitted on the foot 100, said stretch-elastic region 14 has a predefined pretensioning, as a result of which the support arrangement 2 can be held in position relative to the ankle bone 110. Furthermore, the stretch-elastic region 14 facilitates the pretensioning of the attachment element 6 and allows an adaptation to different ankle bone circumferences. Furthermore, stepping into the support arrangement 2 is made easier.

Furthermore, the pretensioning of the stretch-elastic region 14 has the effect that the stiffness of the support arrangement 2 can be increased.

The articulated mounting 5 is here formed by a band and an optional eyelet, which is threaded onto the band, wherein the band is secured to the retaining arrangement 3 at two locations spaced apart from each other and a loop is thus formed. The attachment element 6 is held on the band and thus on the retaining arrangement 3 via the eyelet through which the band runs. In this way, the attachment element 6 can move at least partially along the band relative to the retaining arrangement 3. Moreover, it is possible that the attachment element 6 can be pivoted relative to the retaining arrangement 3.

Compared to the size of the device, the band is in this case so short that the articulated mounting 5 is present substantially at a fixed location of the retaining arrangement 3. This ensures that the introduction of force into the retaining arrangement 3 takes place at a defined position relative to the foot 100, preferably in a limit range between the metatarsus and the front of the foot, and onwards into the foot 100.

Alternatively, the band may also function as an eyelet, wherein the band provides a loop through which the attachment element 6 runs and by means of which said attachment element is diverted. As a further alternative, the mounting 5 may also be provided in the form of a rigid eyelet which is attached to the retaining arrangement 3.

The foot movement limiting device 1 according to FIG. 1 can be worn as a separate device in a conventional shoe. For this purpose, the retaining arrangement 3 can be placed, for example, under a removable insole of the shoe, and, when the shoe is put on, the support arrangement 2 can be brought to the intended position above the ankle bone 110. Alternatively, the foot movement limiting device according to the principle illustrated in FIG. 1 may for example be integrated into a shoe for limiting a foot movement via the ankle joint, as shown for example in FIG. 4.

Figure 2:
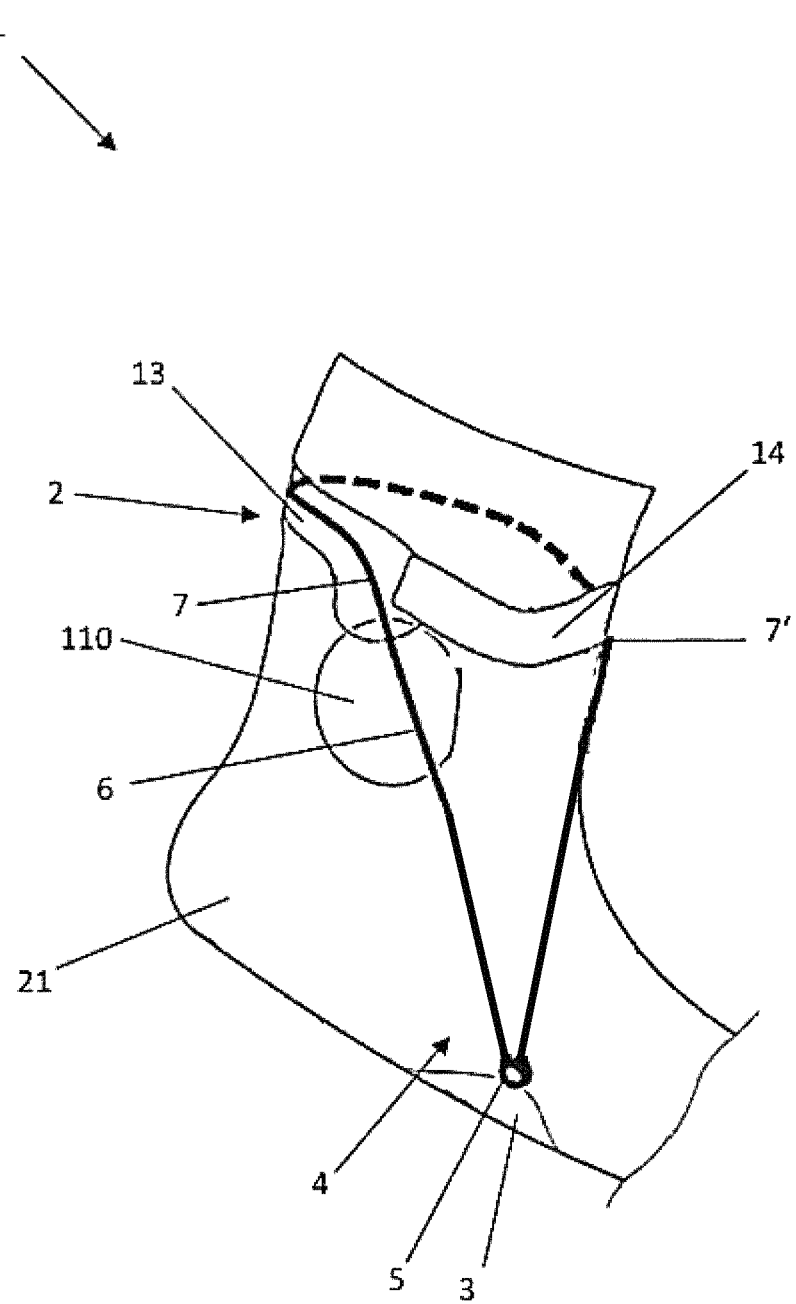
FIG. 2 shows a schematic perspective side view of a foot movement limiting device according to a further embodiment.

FIG. 2 shows a schematic perspective side view of a foot movement limiting device 1 according to a further embodiment. The foot movement limiting device 1 shown here substantially corresponds in its design to the one described with reference to FIG. 1, the main structure being an elastic sock 21 on which both the retaining arrangement 3 and the support arrangement 2 are mounted. The elastic sock 21 can be made available, for example, in the form of a conventional bandage. Once again, the attachment element 6 is held in an articulated manner on the retaining arrangement 3 via the articulated mounting 5 and, as has been described above, is attached via the attachment regions 7, 7' to the support arrangement 2. An advantage of this embodiment is that the foot movement limiting device 1 can be fitted by simply pulling the sock 21 on over the foot 100. Thereafter, the foot can be provided, for example, with a conventional shoe.

Moreover, the articulated mounting 5 is configured here as a pivot joint and is arranged at a fixed location of the retaining arrangement 3. The attachment element 6 is attached to or held on the retaining arrangement 3 so as to be pivotable relative to the retaining arrangement about a pivot axis (not shown here).

Figure 3:
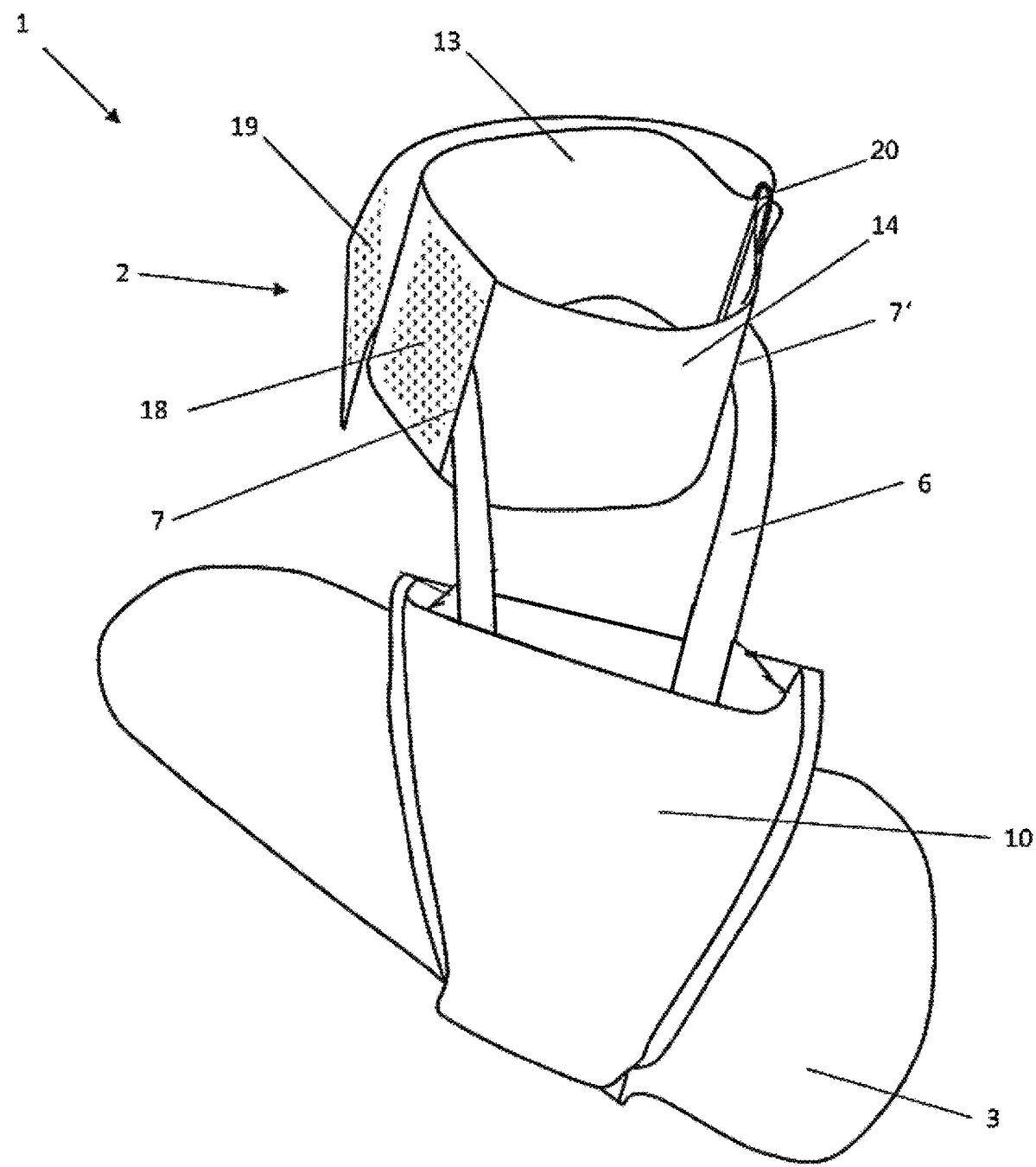
FIG. 3 shows a schematic perspective side view of a foot movement limiting device according to a further embodiment.

FIG. 3 shows a schematic perspective side view of a foot movement limiting device 1 according to a further embodiment which, for example like the device described with reference to FIG. 1, can be worn separately in a conventional shoe or else can be at least partially integrated in a shoe for limiting a foot movement via the ankle joint in order to provide the aforementioned effect.

The foot movement limiting device 1 according to this embodiment has a sole-like retaining arrangement 3. The retaining arrangement 3 can extend substantially over the entire sole region or only over a part of the sole region of the foot.

The support arrangement 2 again has a stretch-resistant region 13 and a stretch-elastic region 14. According to this embodiment, the stretch-resistant region 13 is configured in the form of a stretch-resistant loop which is guided through an eyelet 20 and is turned back in the latter. At the end of the loop, a fastening region 19 is formed which can interact with a corresponding opposite fastening region 18 in order to permit fixing of the loop end at the region near the body. The fastening regions 18, 19 can be configured for example as a hook-and-loop fastener. The anteriorly extending stretch-elastic region 14 is sewn at one end onto the stretch-resistant region 13 and is connected to the latter at the other end via the eyelet 20.

Between the support arrangement 2 and the retaining arrangement 3, an attachment element 6 is once again provided which, as described in FIGS. 1 and 2, is held in an articulated manner on the retaining arrangement 3 via an articulated mounting 5 (not shown in this figure).

A medially extending pocket 10 is connected to the retaining arrangement 3, in which pocket 10 the attachment element 6 is partially received. The pocket 10 in this case makes available a movement space for the attachment element 6, within which the latter can move freely about the movable mounting 5.

Both the pocket 10 and the attachment element 6 are made of a material, in the present case a woven fabric, that in each case has a low coefficient of friction, wherein, optionally, a coefficient of friction of preferably less than or equal to 0.5, preferably less than 0.2 and particularly preferably less than 0.1 is present between the pocket 10 and the attachment element 6. In this way, the free movement of the attachment element 6 in the pocket 10 can be made possible. Alternatively, it is also possible for the material of the pocket 10 and/or the material of the attachment element 6 to be at least partially provided with a low-friction coating.

In the present case, the rear side of the pocket 10, that is to say the inner medial side near the body, is formed in one piece with the retaining arrangement 3 from a stretch-resistant woven fabric. The front of the pocket 10, that is to say the lateral side, is realized by sewing on a further piece of woven fabric. Alternatively, the pocket 10 and the retaining arrangement 3 can also be configured in another way, for example as separate components. The retaining arrangement 3 and the pocket 10 are only optionally connected to each other; they may equally not be connected to each other.

Figure 4:
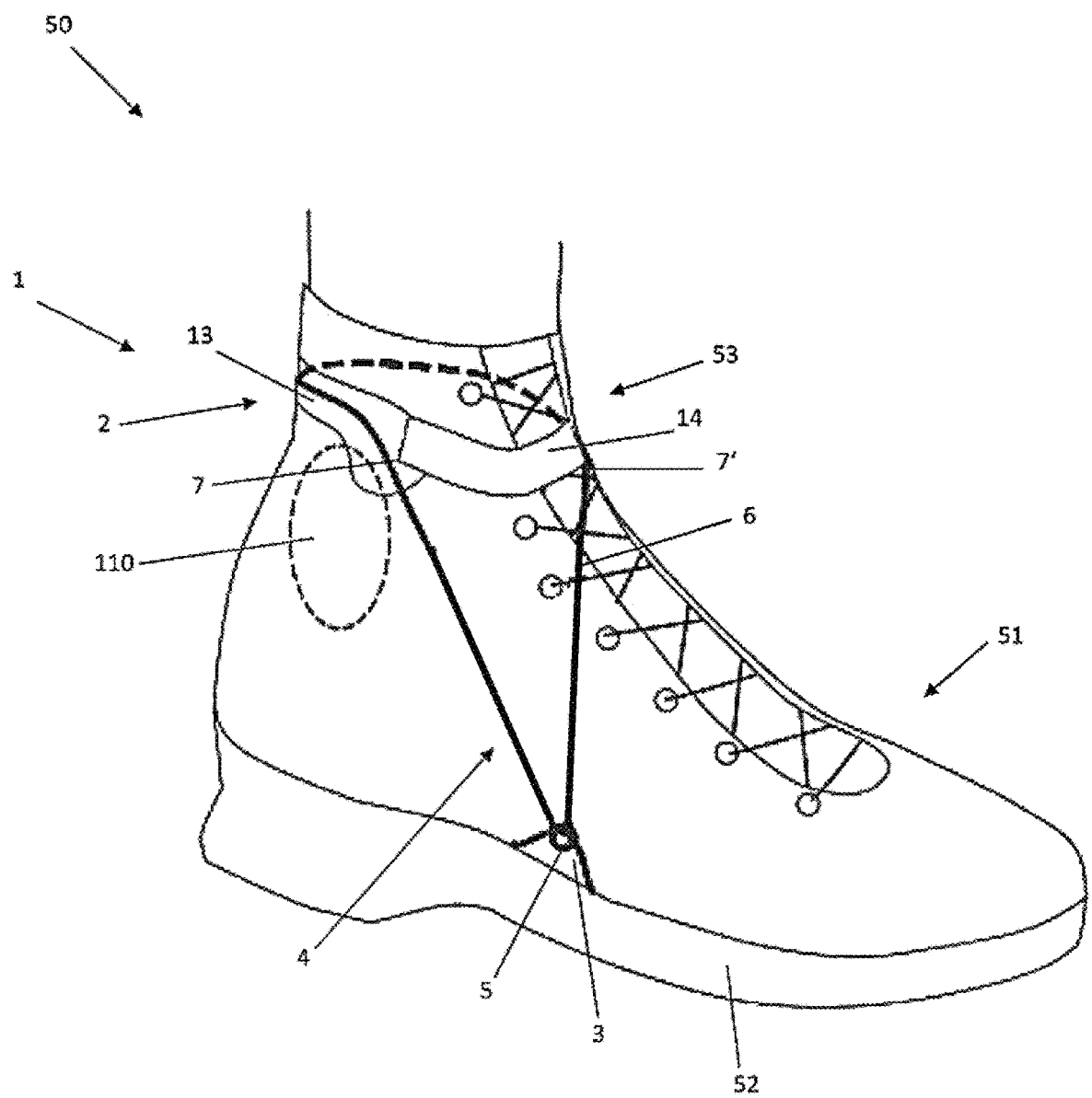
FIG. 4 shows a schematic perspective side view of a shoe according to the disclosure for limiting a foot movement via the ankle joint.

FIG. 4 shows a schematic perspective side view of a shoe 50 according to the disclosure for limiting a foot movement via the ankle joint. The shoe 50 has a sole region 52 and, attached to the sole region 52, a shoe upper 51. Moreover, the shoe 50 comprises a foot movement limiting device 1, which is configured substantially analogously to the embodiment of FIG. 1.

The retaining arrangement 3 is here integrated in the sole region 52. The support arrangement 2 is integrated in a shaft region 53 of the shoe 50. The support arrangement 2 has the retaining regions 7 and 7' at its ends. The attachment element 6 extends from the laterally arranged, first attachment point 7 via the mounting 5 to the medially arranged, second attachment point 7'. Here, the attachment element 6 is, via the articulated mounting 5, arranged movably relative to the retaining arrangement 3 and the sole region 52. On account of the movable attachment of the attachment element 6 to the retaining arrangement 3, the attachment element 6 is movable relative to the shoe upper 51.

In the shoe 50 according to this embodiment, the attachment element 6 is arranged for the most part distally from the ankle bone 110.

Figure 5:
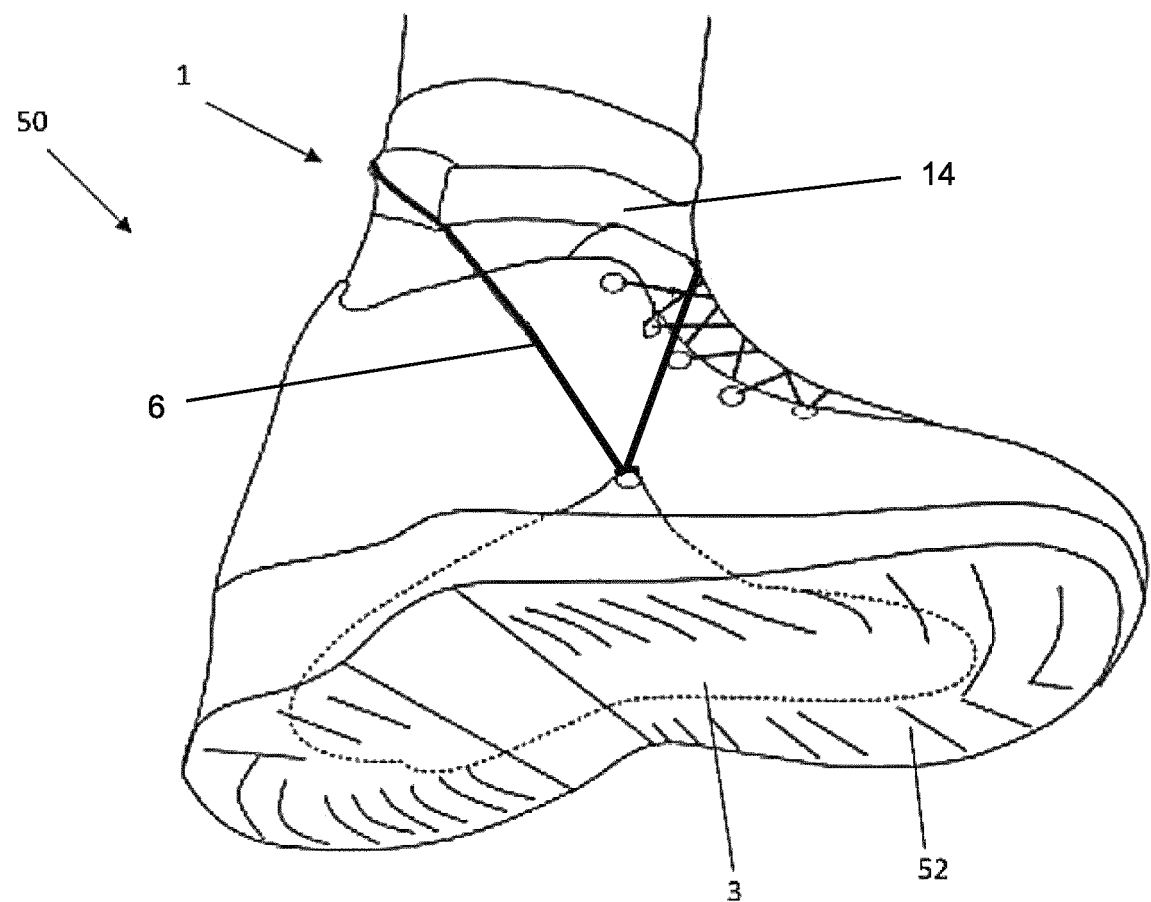
FIG. 5 shows schematically a further perspective side view of the shoe from FIG. 4.

FIG. 5 shows schematically a further perspective side view of the shoe 50 from FIG. 4. Here, the arrangement of the retaining arrangement 3 in the sole region 52 is indicated by means of a broken line.

Figure 6:
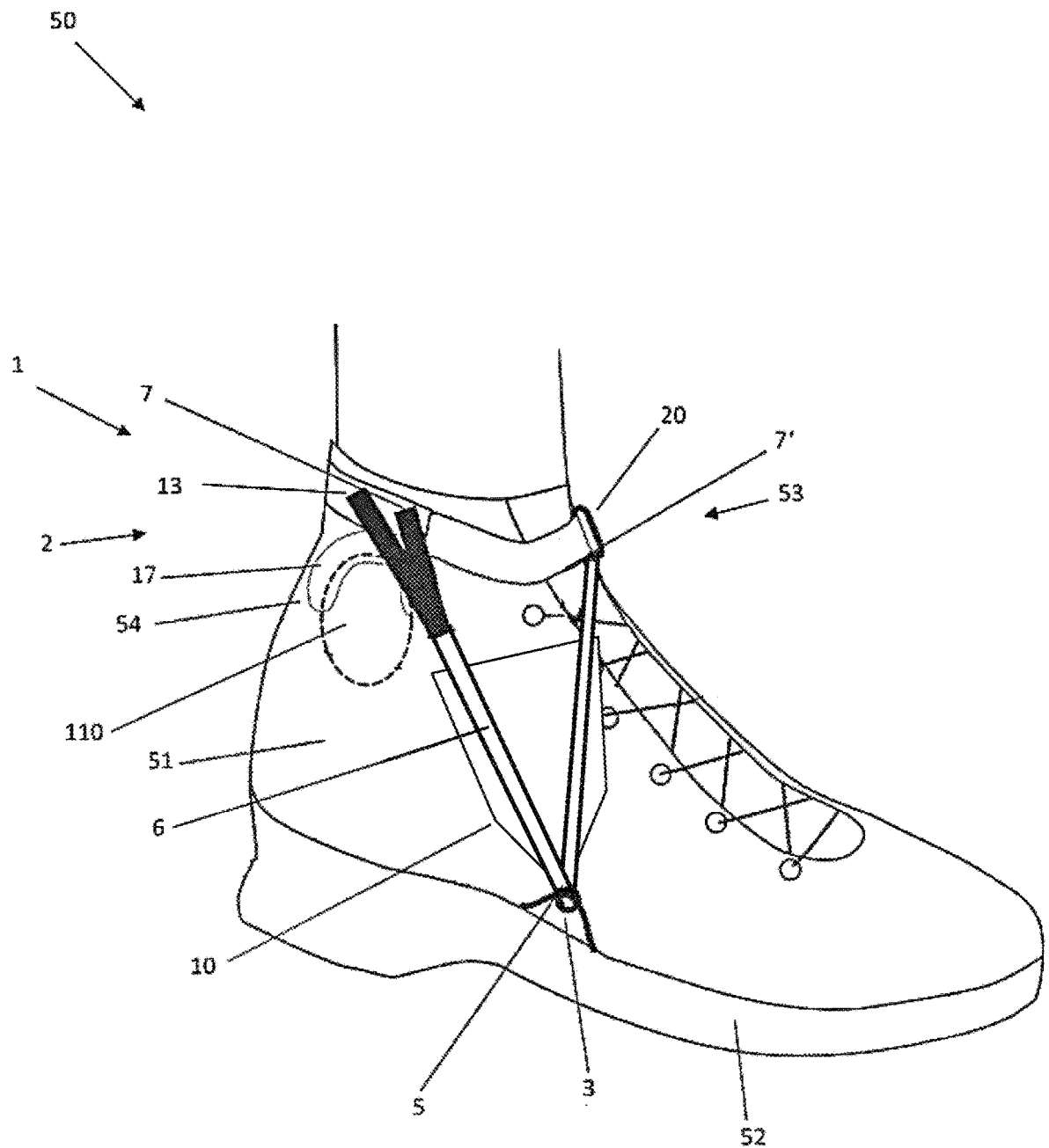
FIG. 6 shows a schematic perspective side view of a shoe according to a further embodiment.

FIG. 6 shows a schematic perspective side view of a shoe 50 according to a further embodiment. The structure of the shoe 50 corresponds substantially to that described with reference to FIG. 4. In addition, the shoe 50 according to FIG. 6 comprises a pocket 10 similar to that described in FIG. 3, wherein, for the sake of a better illustration, the pocket is illustrated as being open.

The pocket 10 is connected fixedly to the shoe upper 51. It again makes available a movement space for the attachment element 6. The attachment element 6 is arranged movably within the limits of the movement space relative to the shoe upper 51.

Moreover, the support region 2 is configured substantially as described with reference to FIG. 3. The stretch-resistant region 13 of the support arrangement 2 can thus be arranged with pretensioning on the body of the person wearing the shoe 50 by being tightened via the eyelet 20 above the ankle bone 110.

In addition, a pad 17 is provided which contributes to maintaining the support arrangement 2 at the intended position of the latter in relation to the body of the person wearing the shoe 50. In addition, the pad 17 provides better support on the ankle bone 110 from the proximal direction.

In order to make available a relative movement of the support arrangement 2 relative to the retaining arrangement 3, the above-described shoes 50 optionally have a flexible deformation portion. Various embodiments of shoes 50 with flexible deformation portions 54 are shown schematically in FIGS. 7 to 11 in which, for reasons of improved clarity, the foot movement limiting devices 1 integrated therein or arranged thereon are not depicted.

Figure 7:
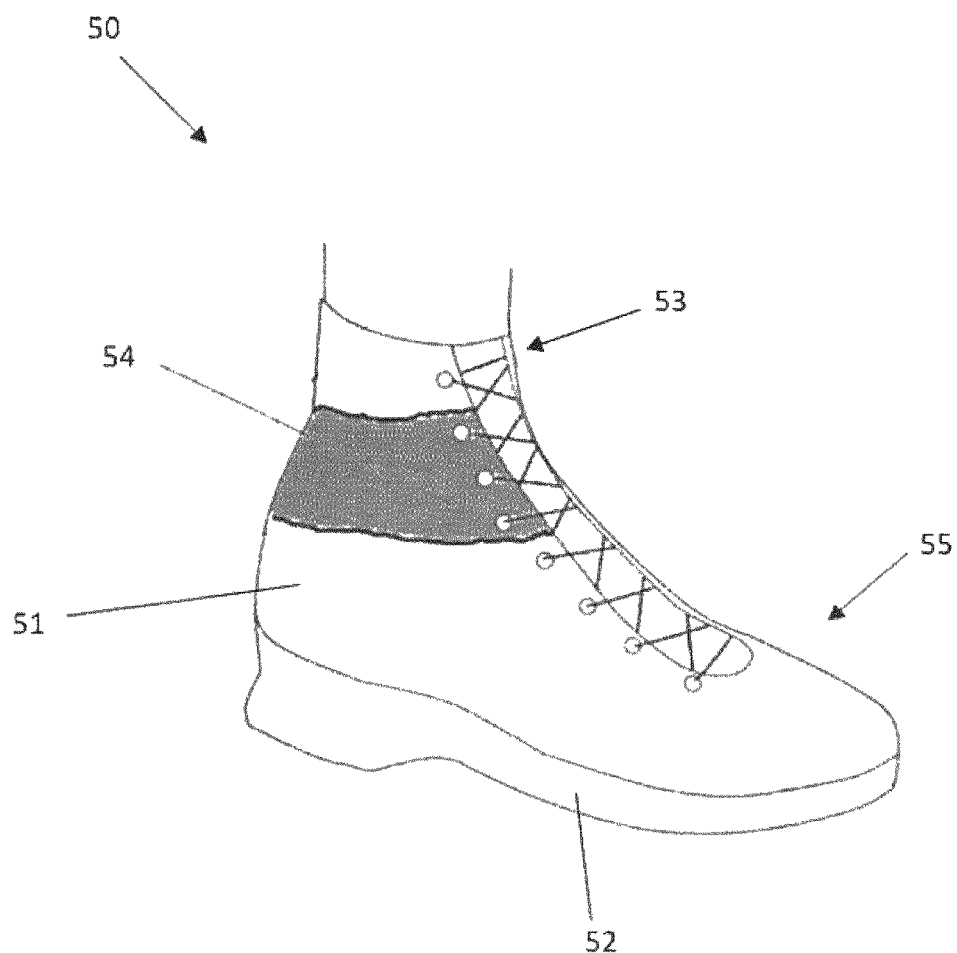
FIGS. 7 to 11 show schematically further embodiments of a shoe for limiting a foot movement via the ankle joint.

In the illustrative embodiment of the shoe 50 according to FIG. 7, the flexible deformation portion 54 extends substantially fully circumferentially between the shaft 53 and a foot region 55 of the shoe upper 51. This results in a particularly high degree of mobility of the support arrangement 2, arranged on the shaft 53, relative to the retaining arrangement 3 arranged in the sole region 52. Preferably, the other regions of the shoe upper 51 are substantially stiff, preferably stretch resistant, analogously to conventional designs.

Figure 8:
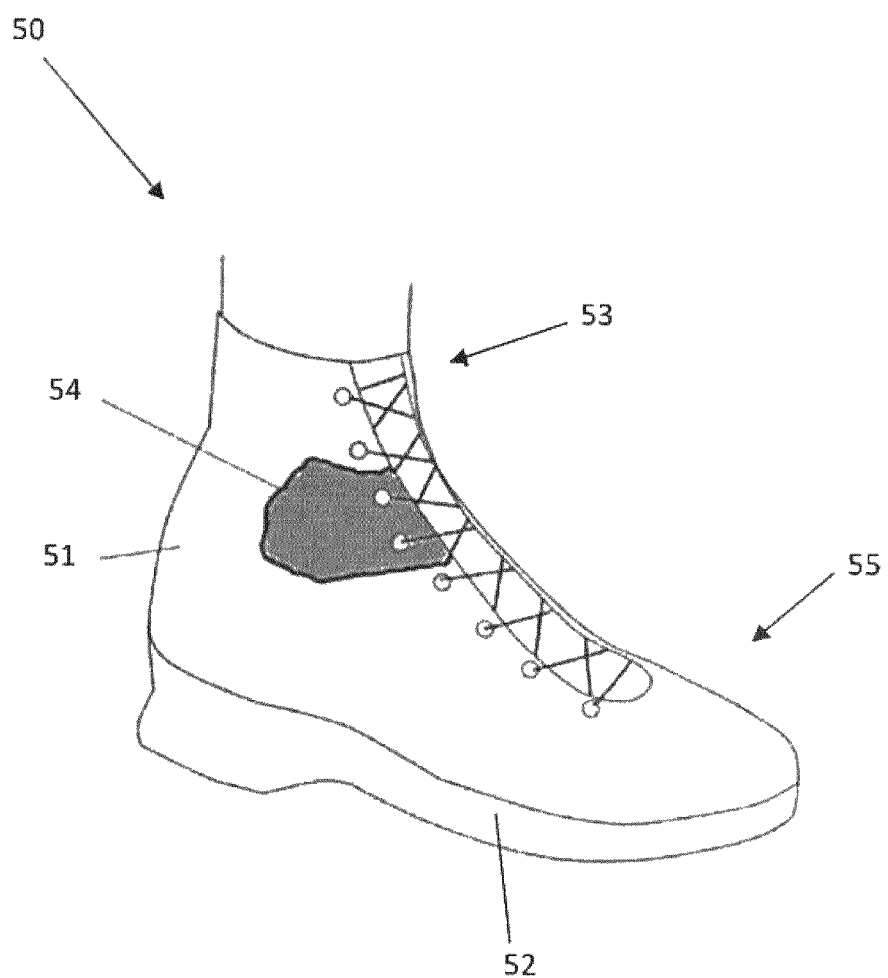
Figure 10:
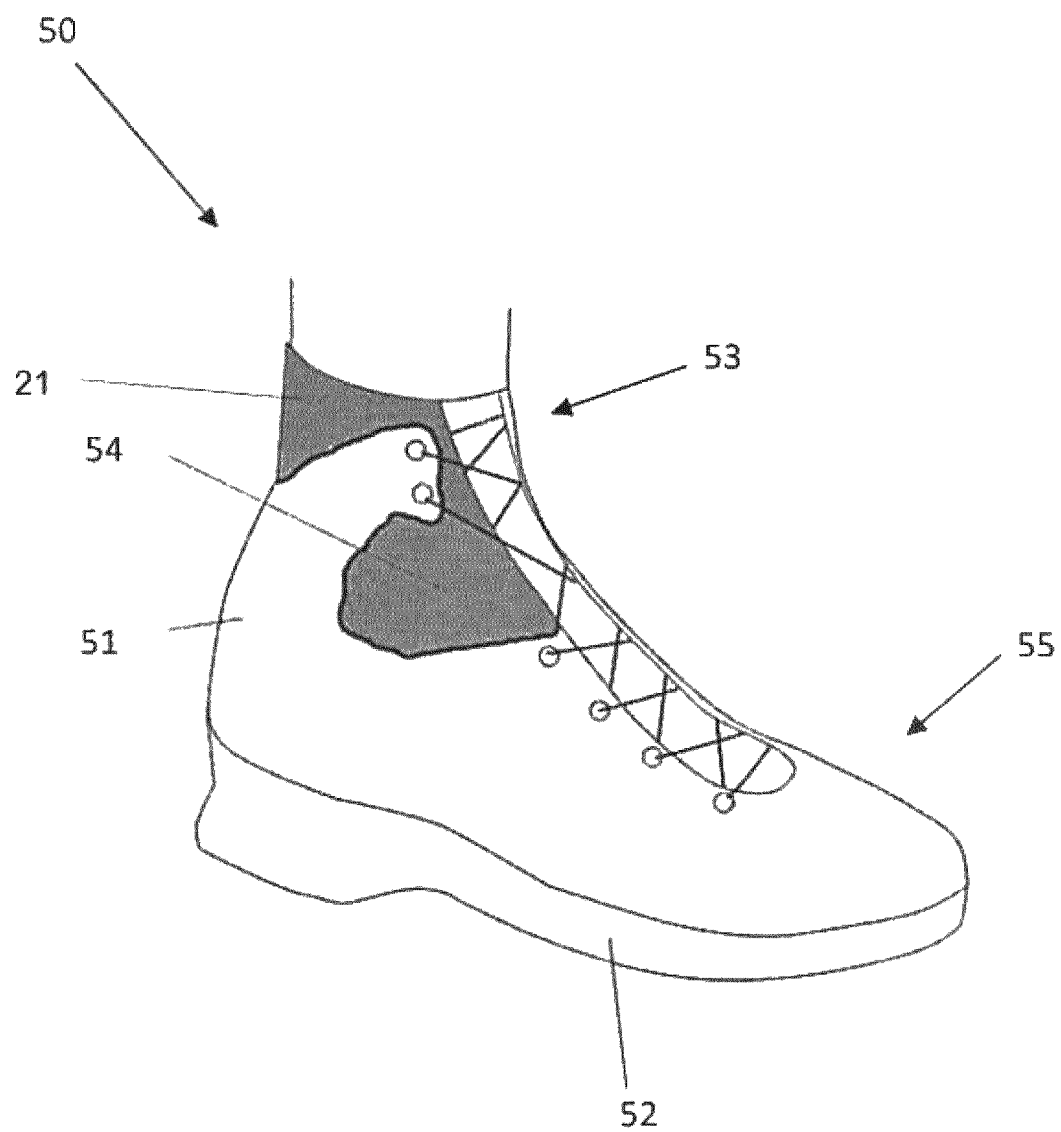

FIG. 8 shows schematically a further embodiment of a shoe 50. In contrast to what is shown in FIG. 10, the flexible deformation portion 54 extends only in a partial region, wherein the flexible deformation portion 54 is arranged in such a way that a relative movement of the support arrangement 2 relative to the retaining arrangement 3 is still permitted. This configuration has the further effect that the shaft region 53 can be additionally supported with respect to the sole region 52 via the heel region of the shoe upper 1, on account of the provision there of a relatively stiff structure of the shoe upper 51.

Figure 9:
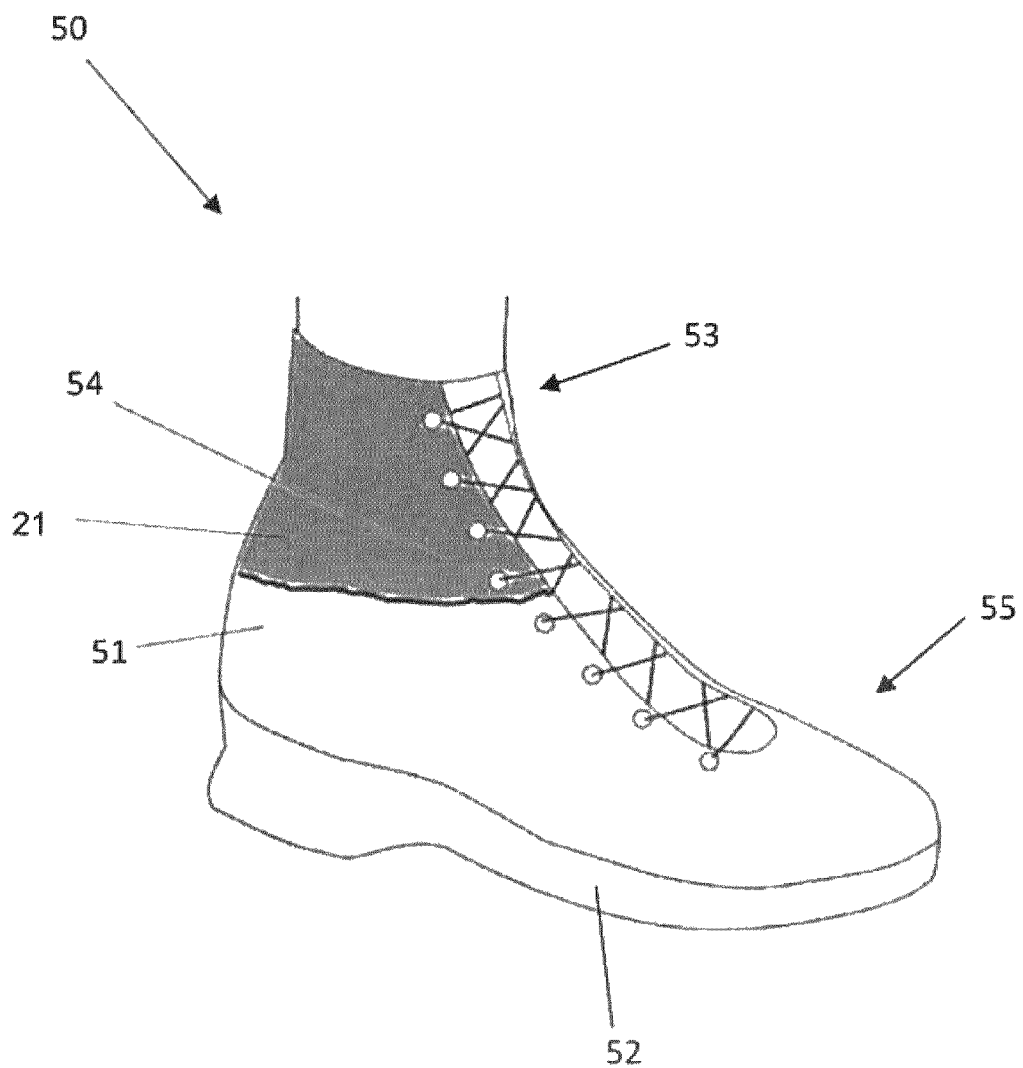

FIG. 9 shows schematically a perspective side view of a shoe 50 according to a further embodiment. Here, the entire upper portion including the complete shaft 53 is flexible. A particularly high degree of wearing comfort is thereby achieved. In shoes 50 according to this illustrative embodiment, the support arrangement 2 is configured preferably as described with reference to FIG. 3. The flexible region 54 can in the present case be realized by a sock region which is configured as part of the shoe 50 and to which the stiff region of the foot region 55 of the shoe upper 51 is connected below the ankle bone 110. Alternatively, the sock region can also extend substantially over the whole shoe 50 and/or can be configured as a sock-shaped inner shoe.

The shoe 50 shown schematically in FIG. 10 is configured substantially like the shoe in FIG. 8, wherein the sensitive deformation portion 54 additionally extends over parts of the shaft 53, as a result of which the wearing comfort is once more enhanced.

Figure 11:
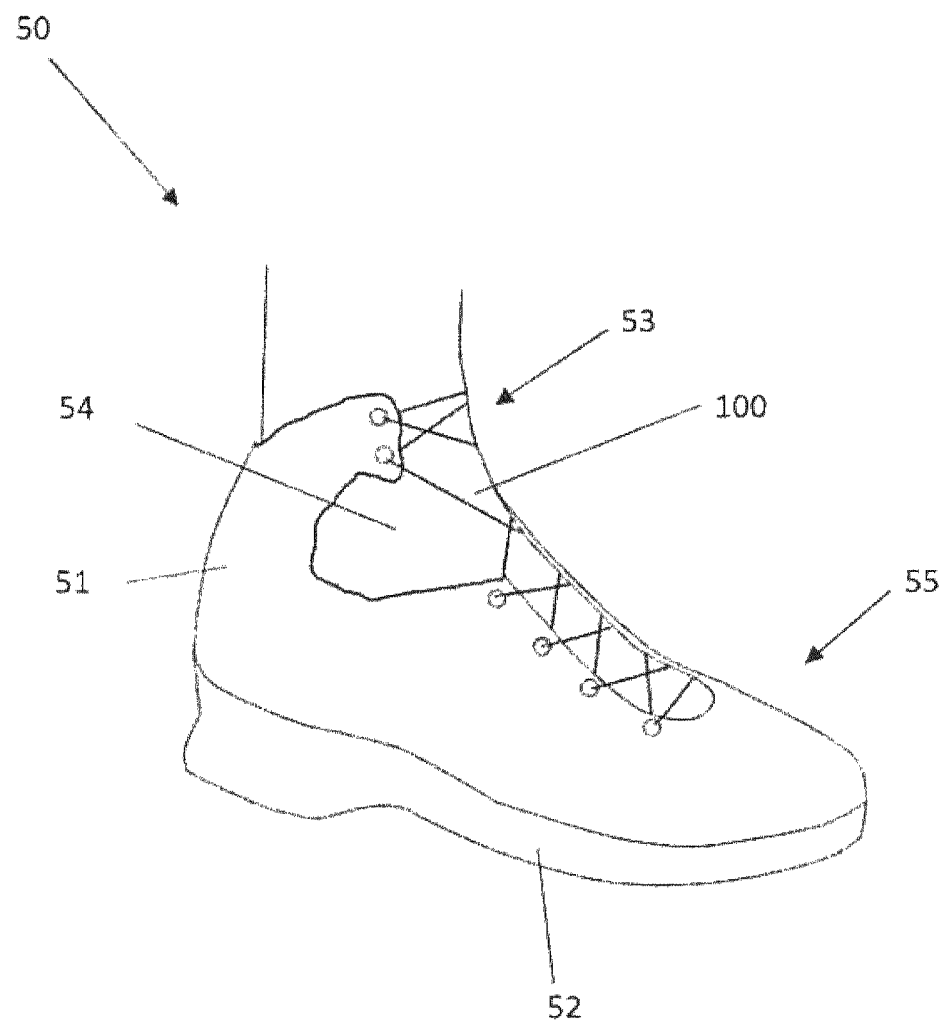

As is shown schematically in FIG. 11, a shoe 50 can optionally also have a flexible deformation portion 54 in the form of a substantially complete material cutout in this region.

Figure 12:
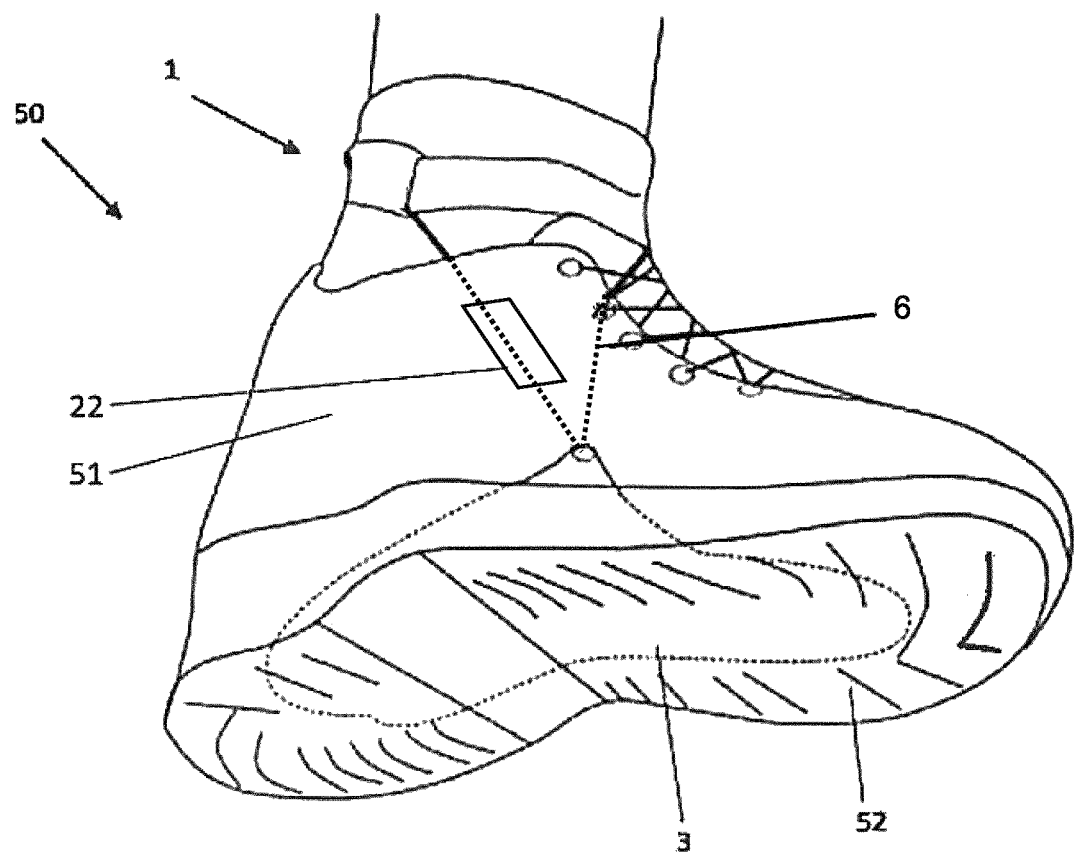
FIG. 12 shows schematically a further embodiment of a shoe for limiting a foot movement via the ankle joint, in which a viewing window is provided in the shoe upper.

FIG. 12 shows schematically a further embodiment of a shoe 50 for limiting a foot movement via the ankle joint. The shoe 50 is configured substantially according to the embodiment shown in FIGS. 4 and 5. However, the attachment element 6 here is additionally integrated in the shoe 50. In other words, the attachment element 6 is arranged inside the shoe 50, underneath an outer cover layer of the shoe upper 51, such that the attachment element 6 is not visible from the outside. In addition, an optional viewing window 22 is provided in the shoe upper 50, through which a free view of a part of the attachment element 6 is obtained from the outside. For better understanding, the covered part of the attachment element 6 is indicated by broken lines.

Figure 13:
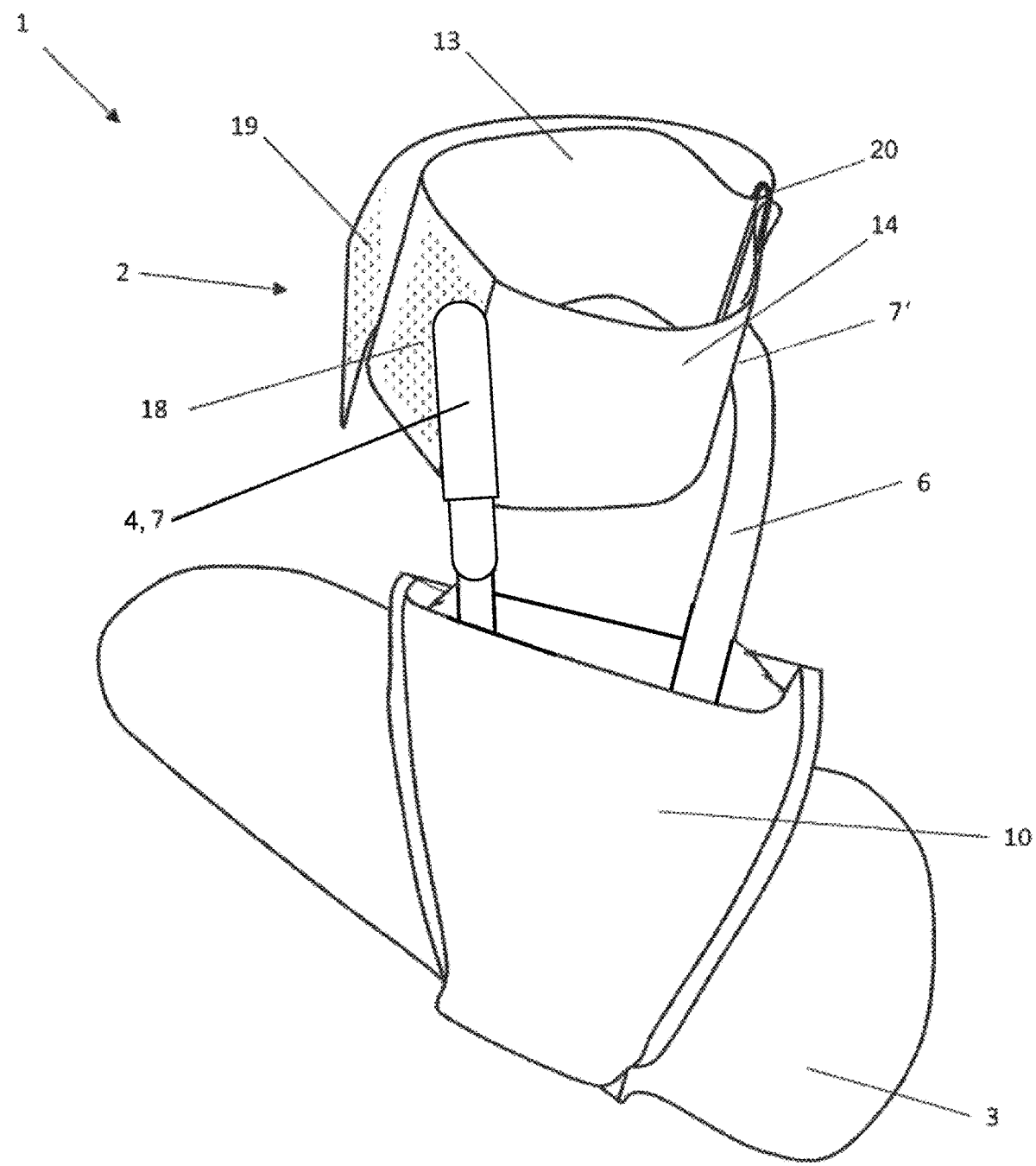
FIG. 13 shows a schematic perspective side view of a foot movement limiting device according to a further embodiment.

FIG. 13 shows a schematic perspective side view of a foot movement limiting device 1 according to a further embodiment, which substantially corresponds to that from FIG. 3. Consequently, the stretch-resistant region 13 of the support arrangement 2 is formed as a loop and the stretch-elastic region 14 is at one end fixedly connected to the stretch-elastic region 13 and, at the other end, has the eyelet 23 through which the loop can be threaded.

Furthermore, the attachment element 6 is held on the support arrangement 2 via a damping element 4. Since the damping element 4 is attached directly to the stretch-resistant region 13, the damping element 4 likewise constitutes the first attachment region 7.

Alternatively, the second attachment region 7' may also be arranged in the region of the eyelet 20 on the stretch-elastic region 14, wherein the eyelet 20 then constitutes a part of the attachment region 7'.

Figure 14:
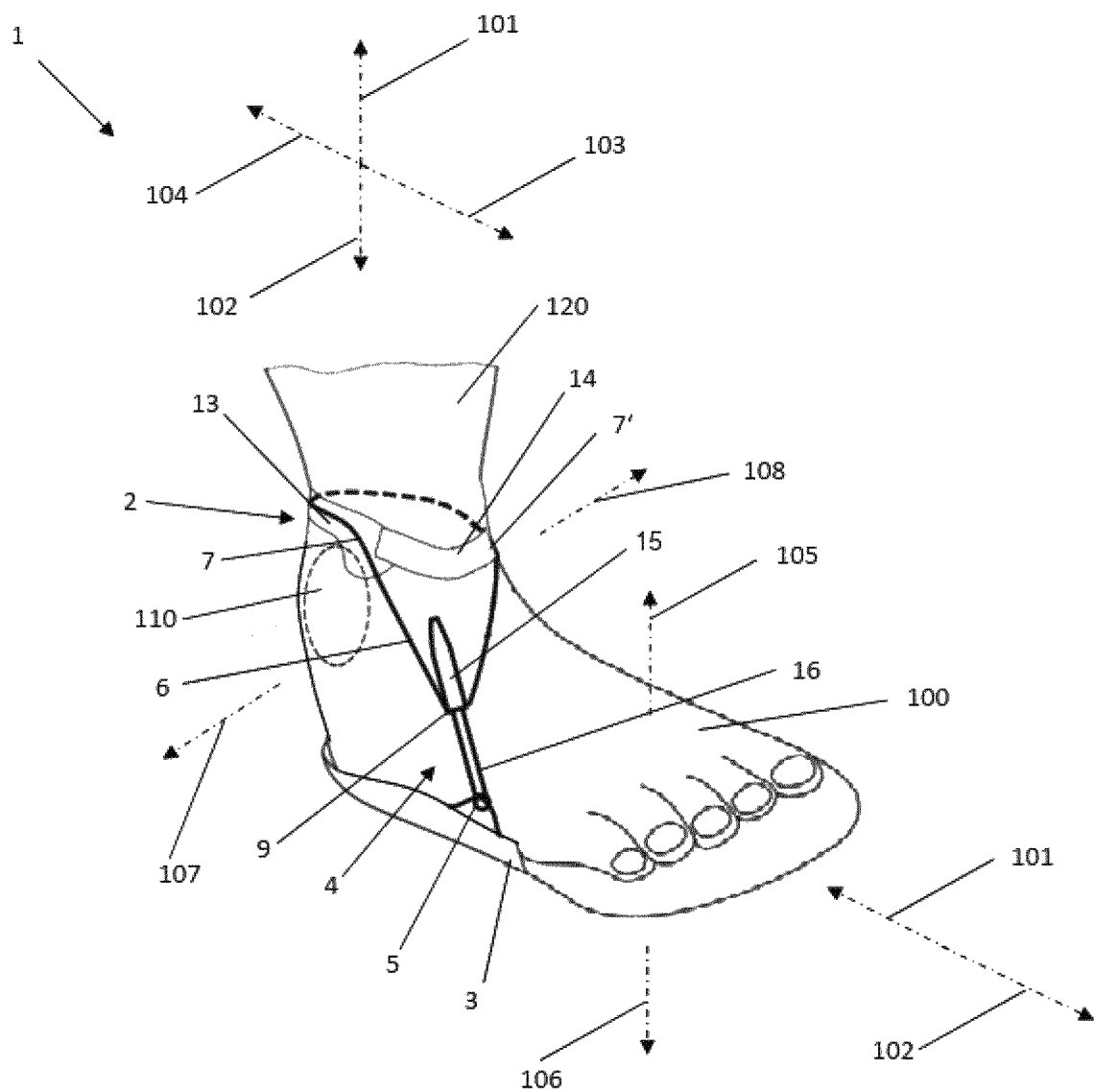
FIG. 14 shows a schematic perspective side view of a foot movement limiting device according to a further embodiment.

FIG. 14 schematically shows a perspective side view of a foot movement limiting device 1 according to a further embodiment, which substantially corresponds to that from FIG. 1. In this embodiment, the attachment element 6 is held on the articulated mounting 5 via a damping element 4.

The damping element 4 is, at its distal end, held articulatedly on the retaining arrangement 3 at the articulated mounting 5. Consequently, the damping element 4 and thus the attachment element 6 are, by means of the articulated mounting 5, movable about the latter relative to the retaining arrangement 3 and thus also relative to foot 100.

The attachment element 6 extends from the support arrangement 2, from a first attachment point 7, via an attachment 9 to the damping element 4 to a second attachment point 7', at which it is again attached to the support arrangement 2. At the attachment 9, the attachment element 6 is displaceably connected to the damping element 4. In other words, by means of the attachment 9, the damping element 4 can be displaced along the attachment element 6.

Where applicable, all the individual features set out in the illustrative embodiments can be combined with one another and/or interchanged, without departing from the scope of the disclosure.

LIST OF REFERENCE SIGNS 1 foot movement limiting device
2 support arrangement
3 retaining arrangement
4 damping element
5 articulated mounting
6, 6' attachment element
7, 7' attachment point
8 central spline
9, 9' attachment
10 pocket
11 sheath
12 guide opening
13 stretch-resistant region
14 stretch-elastic region
15 receptacle
16 tensioning element
17 pad
18 fastening region
19 fastening region
20 eyelet
21 sock
22 viewing window
50 shoe
51 shoe upper
52 sole region
53 shaft region
54 flexible deformation portion
55 foot region
100 foot
101 proximal
102 distal
103 posterior
104 anterior
105 dorsal
106 plantar
107 lateral
108 medial
110 ankle bone

The invention claimed is:

1. A foot movement limiting device for limiting a foot movement via the ankle joint, comprising a support arrangement for supporting on a lower leg or from proximally on the ankle bone, a retaining arrangement for retention on a foot and at least one attachment element for limiting a relative movement between the support arrangement and the retaining arrangement,
wherein the at least one attachment element is attached to the support arrangement at two different attachment points, and the at least one attachment element is, at a point between the two attachment points, held by means of an articulated mounting on the retaining arrangement,
wherein the articulated mounting is configured in such a way that the attachment element is attached to the retaining arrangement so as to be displaceable relative to the latter within a predefined range,
wherein the support arrangement comprises a stretch-resistant region extending posteriorly around from a lateral side, from the first attachment point, at least to a medial side, to the second attachment point, or the support arrangement comprises a stretch-resistant region extending anteriorly around from a lateral side, from the first attachment point, at least to a medial side, to the second attachment point, wherein the stretch-resistant region is connected at its ends by a stretch-elastic region, wherein the stretch-elastic region extends between the first attachment point and the second attachment point counter to the stretch-resistant region, and
wherein the stretch-elastic region extends between the first attachment point and the second attachment point counter and not-coextensive to the posteriorly extending stretch-resistant region by extending anteriorly around from a lateral side, from the first attachment point, at least to a medial side, to the second attachment point; or
the stretch-elastic region extends between the first attachment point and the second attachment point counter and not-coextensive to the anteriorly extending stretch-resistant region by extending posteriorly around from a lateral side, from the first attachment point, at least to a medial side, to the second attachment point.

2. The foot movement limiting device as of claim 1, wherein the attachment points are positioned relative to the attachment element in such a way that a retaining force arising in the attachment element as a result of a foot movement via the ankle joint is divided into a laterally and proximally acting component and a medially and proximally acting component.

3. The foot movement limiting device of claim 1, wherein the at least one attachment element is held by way of a damping element on the support arrangement or the retaining arrangement.

4. The foot movement limiting device of claim 3, wherein the damping element is fastened to the stretch-resistant region of the support arrangement.

5. The foot movement limiting device of claim 3, wherein the damping element is held displaceably on the at least one attachment element, wherein the damping element is attached to the attachment element between the two attachment points.

6. The foot movement limiting device of claim 3, further comprising a second attachment element, wherein
the first attachment element, relative to a central spline of the damping element, is attached to the damping element at a distance from the central spline on a first side of the damping element, and
the second attachment element, relative to the central spline of the damping element is attached to the damping element at a distance from the central spline on a second side of the damping element,
wherein the distance of the attachments of first attachment element and second attachment element to the damping element is substantially identical relative to the central spline and,
wherein the first attachment element and the second attachment element are configured together as an individual part.

7. The foot movement limiting device of claim 6, wherein the central spline comprises a central axis, and the first attachment element of the damping element is attached slidably to the damping element at a distance from the central axis on a first side of the damping element, and
the second attachment element of the damping element is attached slidably to the damping element at a distance from the central axis on a second side of the damping element,
wherein the distance of the attachments of first attachment element and second attachment element to the damping element is substantially identical relative to the central axis, and
wherein the first attachment element and the second attachment element are configured together as the individual part, and the individual part is turned back and guided slidably at the first attachment point or the second attachment point.

8. The foot movement limiting device of claim 6, wherein a pocket is provided for at least partially receiving the attachment element and/or the damping element, and wherein the attachment element and/or damping element received in the pocket is arranged in the pocket in such a way as to be movable relative to the latter.

9. The foot movement limiting device of claim 8, wherein the pocket is connected to the support arrangement or the retaining arrangement.

10. The foot movement limiting device as claimed in claim 6, wherein the damping element has a receptacle which is filled with a damping fluid and in which a pull-out body is received movably relative to the latter, wherein the pull-out body is connected to a tensioning element extending in a pull-out direction from the receptacle, wherein the receptacle is arranged proximally and the tensioning element extends distally from the receptacle, wherein the tensioning element is connected in an articulated manner to the retaining arrangement, wherein the attachment of the at least one attachment element to the receptacle is arranged at a distal end of the receptacle.

11. The foot movement limiting device as claimed in claim 6, wherein the attachment element and/or the damping element is held in an articulated manner on a pivot joint and/or ball joint arranged at a fixed location of the retaining arrangement and forms an articulated mounting, and/or the articulated mounting is configured in such a way that the attachment element and/or the damping element is attached to the retaining arrangement so as to be displaceable relative to the latter within a predefined range, wherein the retaining arrangement has a band which is fastened to the retaining arrangement at two locations spaced apart from each other, wherein the attachment element and/or the damping element is held on the band via an eyelet or loop through which the band runs.

12. The foot movement limiting device of claim 1, wherein a volume body is arranged above the lateral malleolus, in order to bear from proximally on the lateral malleolus, and/or a volume body, preferably a pad, is arranged above the medial malleolus, in order to bear from proximally on the medial malleolus.

13. A shoe for limiting a foot movement via the ankle joint, comprising a sole region and, attached to the sole region, a shoe upper, the shoe further comprising a foot movement limiting device of claim 1.

14. The shoe of claim 13, wherein the retaining arrangement is integrated in the sole region and the support arrangement is integrated in a shaft region of the shoe upper, wherein the attachment element is movable relative to the shoe upper.

15. The shoe of claim 13, wherein the foot movement limiting device is integrated substantially completely in the shoe.

16. The shoe of claim 13, further comprising a flexible deformation portion in order to permit a relative movement of the support arrangement relative to the retaining arrangement.

17. The shoe of claim 13, wherein a pocket is connected fixedly to the shoe upper and is integrated in the shoe upper, and/or wherein an attachment element and/or a damping element is arranged substantially distally from the ankle bone, and/or wherein a window is provided on the shoe upper, configured in such a way that a view of at least a part of the attachment element and/or of the damping element is provided from outside the shoe.

18. The foot movement limiting device of claim 1 wherein a same attachment element of the at least one attachment element is attached to the support arrangement at two different attachment points, and the same attachment element is held by means of the articulated mounting on the retaining arrangement at the point between the two attachment points at only one point.

* * * * *